US012601015B2

(12) United States Patent
Chen et al.

(10) Patent No.: US 12,601,015 B2
(45) Date of Patent: Apr. 14, 2026

(54) ALLELE, MOLECULAR MARKER, AND PRIMER PAIR OF RICE HPS1 GENE, AND APPLICATIONS THEREOF

(71) Applicant: SICHUAN AGRICULTURAL UNIVERSITY, Chengdu City (CN)

(72) Inventors: Xuewei Chen, Chengdu City (CN); Jing Wang, Chengdu City (CN); Haicheng Liao, Chengdu City (CN); Yu Fang, Chengdu City (CN); Yingjie Wei, Chengdu City (CN); Jiankui Cha, Chengdu City (CN); Min He, Chengdu City (CN); Weitao Li, Chengdu City (CN); Junjie Yin, Chengdu City (CN); Xiaobo Zhu, Chengdu City (CN)

(73) Assignee: SICHUAN AGRICULTURAL UNIVERSITY, Chengdu City (CN)

( * ) Notice: Subject to any disclaimer, the term of this patent is extended or adjusted under 35 U.S.C. 154(b) by 0 days.

(21) Appl. No.: 19/252,300

(22) Filed: Jun. 27, 2025

(65) Prior Publication Data

US 2025/0327139 A1 Oct. 23, 2025

Related U.S. Application Data

(63) Continuation of application No. PCT/CN2025/075698, filed on Feb. 5, 2025.

(30) Foreign Application Priority Data

Feb. 26, 2024 (CN) .......................... 202410207238.5

(51) Int. Cl.
| | |
|---|---|
| *C12Q 1/68* | (2018.01) |
| *A01H 1/04* | (2006.01) |
| *C07H 21/04* | (2006.01) |
| *C12Q 1/6895* | (2018.01) |

(52) U.S. Cl.
CPC .......... *C12Q 1/6895* (2013.01); *A01H 1/045* (2021.01); *C12Q 2600/13* (2013.01); *C12Q 2600/156* (2013.01)

(58) Field of Classification Search
None
See application file for complete search history.

(56) References Cited

U.S. PATENT DOCUMENTS

2007/0039076 A1* 2/2007 Boukharov ............ A01G 22/22
                                                          800/278
2017/0009249 A1 1/2017 Goossens et al.

FOREIGN PATENT DOCUMENTS

| CN | 104610439 A | 5/2015 |
|---|---|---|
| CN | 115725775 A | 3/2023 |
| CN | 117821658 A | 4/2024 |

OTHER PUBLICATIONS

NEB catalog (1998/1999), pp. 121, 284. (Year: 1998).*
Notice of first Office action dated Aug. 5, 2024 in SIPO application No. CN202410207238.5, 16 pages.
Retrieval report-First search dated Aug. 1, 2024 in SIPO application CN202410207238.5, 5 pages.
Notification to Grant Patent Right for Invention dated Aug. 29, 2024 in SIPO application CN202410207238.5, 4 pages.
Retrieval report-Supplementary search dated Aug. 19, 2024 in SIPO application CN202410207238.5, 4 pages.
International Search Report issued in corresponding PCT Application No. PCT/CN2025/075698 dated Apr. 28, 2025, 9 pages.
Mingguang Lei et al., "Genetic and genomic evidence that sucrose is a global regulator of plant responses to phosphate starvation in *Arabidopsis*", Plant Physiol, Feb. 23, 2011, pp. 1116-1130, vol. 156, Issue 3, 15 pages.
Shi Chan et al., "Evaluation of the resistance spectrum of three important rice cultivars against blast disease caused by Magnaporthe oryzae and correlation analysis among evaluation indexes, Journal of Plant Protection", Aug. 15, 2014, pp. 390-395, vol. 41, Issue 4, 6 pages.
Koji Miyamoto et al., "Identification of an e-box motif responsible for the expression of jasmonic acid-induced chitinase gene OSChia4a in rice", Journal of Plant Physiology, Apr. 15, 2012 , pp. 621-627, vol. 169, Issue 6, ISSN: 0176-1617, Table 2, 7 pages.

* cited by examiner

*Primary Examiner* — Jeanine A Goldberg
(74) *Attorney, Agent, or Firm* — Cooper Legal Group LLC

(57) ABSTRACT

An allele, a molecular marker, a primer pair of rice HPS1 gene, and applications thereof are provided. An allele of the rice HPS1 gene is provided. The allele is a natural excellent allele of the HPS1 gene. Furthermore, a natural structural variation of 192 bp fragment deletion in the promoter of the allele of HPS1 gene is identified from rice resources with excellent agronomic traits, such as 93-11 variety. Based on this, a molecular marker primer for assisted breeding is developed.

1 Claim, 13 Drawing Sheets

Specification includes a Sequence Listing.

SEQUENCE LISTING

```
Sequence total quantity: 9
SEQ ID NO: 1              moltype = DNA  length = 1500
FEATURE                  Location/Qualifiers
source                   1..1500
                         mol_type = other DNA
                         organism = synthetic construct
SEQUENCE: 1
taatttgttg ggattagtca tcgtcatgta acgacttgca caacaaactc atttctaatt   60
tgctctctct ttgttttgcc gccgcccacg caatgtatat atctactgca gattccttcc   120
atgcatgcat cttaattaac ttctccgaat tcatggattc caaatgaata atgaataaga   180
tgctaagcta ggtttaccaa ttaattggct aattggcaac caaatggcta atcatcatca   240
ccatcatggc atcatcatca aattttctaa acgttgcacc ggaaaatcaa cctagactgg   300
aattccttcc aatccttcgc tatagctagc tagctaccac aacgatccaa aagtttgtc   360
aaatatttag aacggggata gctaggcagt gtcgacgaag atgtgatgtg atctctgaat   420
atctgaaccg tcgtctgatc cacaaaaagc ttcccggctc cggacgctag ctgctccatc   480
ccatcaattc tctccattct cgcttgcatc cagccaaacc aaattgaccg tggactgatc   540
acatttatac tgctacatca tccgccgtta atatatattt tgagagacca tatcattgat   600
agatacatgc atgcatccta ctaattcgcc cagatcaacg gccggtctcg agacgtactc   660
gccggtaatt tgccggaaat tgttatacgt tttccaaggg aagatgtctt tttttatgcc   720
atctaaatag ttatgaaaca ttttgattaa ttttcttttc acgggataga ttaatatacg   780
atatgtatca ctctgtaaat atgcatgttc agaatttcaa cccctacatg ttattgtaaa   840
atgataaata tgactgtgaa aatgcgtaga ctagtagagt ttttttttc attttgttac   900
aatgcaactt ggtattcatg tttgtaaagt aatatatctc atattaatat atcttataaa   960
aaattatatt tttaagttat tttggtggct tacaagaaac gatgggatcg atatattcct   1020
tcgaggggaa aacaaggaac atttcccaat ttgccattaa tctactctca ctcatcacag   1080
tcatcatgct agttgatctg cacgctgatc cgatccggcc ggaaatttcg aacttaatta   1140
gcacgtggat taattagttg gcaaaagcta agtacaagtc attgtgtggt caattgatcg   1200
actgatctgt tgctccccgc ttctgcggct ttcattggct ataaatacgc agatatgtgc   1260
tcactgccta gctaccagtc ttgcatctct aactatatat acacatacat gtagcatcct   1320
gctccatctt aactagctac tactagtgat gagcagaatc aacctcatgc agtaatatgc   1380
tgtgctgatc gaattaattt acacatatat agatagatag atagatagat cgttcgacca   1440
atcgagctag cttgagcaaa ctgattgacc tggtgaagtg gtataattaa cgagcagatc   1500

SEQ ID NO: 2              moltype = DNA  length = 1308
FEATURE                  Location/Qualifiers
source                   1..1308
                         mol_type = other DNA
                         organism = synthetic construct
SEQUENCE: 2
taatttgttg ggattagtca tcgtcatgta acgacttgca caacaaactc atttctaatt   60
tgctctctct ttgttttgcc gccgcccacg caatgtatat atctacggaa ttccttccaa   120
tccttcgcta tagctagcta gctaccacaa cgatccaaaa gttttgtcaa atatttagaa   180
cggggatagc taggcagtgt cgacgaagat gtgatgtgat ctctgaatat ctgaaccgta   240
gtctgatcca caaaaagctt cccggctccg gacgctagct gctccatccc atcaattctc   300
tccattctcg cttgcatcca gccaaaccaa attgaccgtg gactgatcac atttatactg   360
ctacatcatc cgccgttaat atatattttg agagaccata tcattgatag atacatgcat   420
gcatcctact aattcgccca gatcaacggc cggtctcgag acgtactcgc cggtaattgt   480
ccggaaattg ttatacgttt tccaagggaa gatgtctttt tttatgccat ctaaatagtt   540
atgaaacatt ttgattaatt ttcttttcac gggatagatt aatatacgat atgtatcact   600
ctgtaaatat gcatgttcag aatttcaacc cctacatgtt attgtaaaat gataaatatg   660
actgtgaaaa tgcgtagact agtagagttt ttttttcat tttgttacaa tgcaacttgg   720
tattcatgtt tgtaaagtaa tatatctcat attaatatat cttataaaaa attatatatt   780
taagttattt ggtggcttac aagaaacga tgggatcgat atattccttc gagggaaaa   840
caaggaacat ttcccaattt gccattaatc tactctcact catcacagtc atcatgctag   900
ttgatctgca cgctgatccg atccggcggg aaatttcgaa cttaattagc acgtggatta   960
attagttggc aaaagctaag tacaagtcat tgtgtggtca attgatctgt tgtctgttg   1020
ctccccgctt ctgcggcttt cattggctat aaatacgcag atatgtgctc actgcctagc   1080
taccagtctt gcatctctaa ctatatatac acacatgt agcatcctgc tccatcttaa   1140
ctagctacta ctagtgatga gcagaatcaa cctcatgcag taatatgctg tgctgatcga   1200
attaatttac acatatatag atagatagat agatagatcg ttcgaccaat cgagctagct   1260
tgagcaaact gattgacctg gtgaagtggt ataattaacg agcagatc              1308

SEQ ID NO: 3              moltype = DNA  length = 439
FEATURE                  Location/Qualifiers
source                   1..439
                         mol_type = other DNA
                         organism = synthetic construct
SEQUENCE: 3
cgtcatgtaa cgacttgcac aacaaactca tttctaattt gctctctctt tgttttgccg   60
```

-continued

```
ccgcccacgc aatgtatata tctactgcag attccttcca tgcatgcatc ttaattaact   120
tctccgaatt catggattcc aaatgaataa tgaataagat gctaagctag gtttaccaat   180
taattggcta attggcaacc aaatggctaa tcatcatcac catcatggca tcatcatcaa   240
attttctaaa cgttgcaccg gaaaatcaac ctagactgga attccttcca atccttcgct   300
atagctagct agctaccaca acgatccaaa agttttgtca aatatttaga acggggatag   360
ctaggcagtg tcgacgaaga tgtgatgtga tctctgaata tctgaaccgt cgtctgatcc   420
acaaaaagct tcccggctc                                                439
```

```
SEQ ID NO: 4              moltype = DNA   length = 21
FEATURE                   Location/Qualifiers
source                    1..21
                          mol_type = other DNA
                          organism = synthetic construct
SEQUENCE: 4
cgtcatgtaa cgacttgcac a                                             21
```

```
SEQ ID NO: 5              moltype = DNA   length = 20
FEATURE                   Location/Qualifiers
source                    1..20
                          mol_type = other DNA
                          organism = synthetic construct
SEQUENCE: 5
gagccgggaa gctttttgtg                                               20
```

```
SEQ ID NO: 6              moltype = DNA   length = 40
FEATURE                   Location/Qualifiers
source                    1..40
                          mol_type = other DNA
                          organism = synthetic construct
SEQUENCE: 6
ttgatatcga attcctgcag taatttgttg ggattagtca                         40
```

```
SEQ ID NO: 7              moltype = DNA   length = 40
FEATURE                   Location/Qualifiers
source                    1..40
                          mol_type = other DNA
                          organism = synthetic construct
SEQUENCE: 7
gctctagaac tagtggatcc gatctgctcg ttaattatac                         40
```

```
SEQ ID NO: 8              moltype = DNA   length = 20
FEATURE                   Location/Qualifiers
source                    1..20
                          mol_type = other DNA
                          organism = synthetic construct
SEQUENCE: 8
ggcaacaacg gcttcatgtg                                               20
```

```
SEQ ID NO: 9              moltype = DNA   length = 20
FEATURE                   Location/Qualifiers
source                    1..20
                          mol_type = other DNA
                          organism = synthetic construct
SEQUENCE: 9
tgaggtggtg ctcaatctgc                                               20
```

ALLELE, MOLECULAR MARKER, AND PRIMER PAIR OF RICE HPS1 GENE, AND APPLICATIONS THEREOF

CROSS-REFERENCE TO RELATED APPLICATIONS

This application is a continuation of International Patent Application No. PCT/CN2025/075698, filed Feb. 5, 2025, and claims priority of Chinese Patent Application No. 202410207238.5, filed on Feb. 26, 2024. The entire contents of International Patent Application No. PCT/CN2025/075698 and Chinese Patent Application No. 202410207238.5 are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: SequenceListing.xml
Creation date: Jun. 24, 2025
Byte size: 12,209

TECHNICAL FIELD

The present disclosure relates to the field of crop breeding, and in particular relates to an allele, a molecular marker, a primer pair of rice hydrogen peroxide sensor 1 (HPS1) gene, and applications thereof.

BACKGROUND

Rice is one of the most important food crops in the world and a staple food for the Chinese population. Therefore, the stability of rice yield is crucial for ensuring food security. Various natural diseases, such as rice blast, severely threaten rice production safety. Discovering disease-resistant rice resources and disease-resistant genes, and conducting disease-resistant breeding, are the most effective and environmentally friendly means to combat rice diseases. Domestic and international scholars have conducted extensive research on disease resistance mechanism and pathogenic mechanism of rice, forming a preliminary theoretical framework for rice-pathogen interactions. Under the guidance of relevant theories, breeders have developed a batch of new disease-resistant rice varieties, which have somewhat alleviated the threat of diseases. However, the dominant pathogenic populations of different pathogens, including *Magnaporthe oryzae*, may rapidly change and frequently turnover, leading to the rapid weakening or even loss of resistance in the bred disease-resistant varieties. Different alleles may have different functions, and mining disease-resistant alleles may uncover natural resistance alleles that may be directly applied to actual crop production without relying on transgenic technology. Therefore, there is an urgent need for effective technologies in rice breeding to identify more excellent alleles to enhance rice resistance to different pathogens.

SUMMARY

An objective of the present disclosure is to provide an allele, a molecular marker, a primer pair of rice hydrogen peroxide sensor 1 (HPS1) gene, and applications thereof, to address the issues in the prior art. The present disclosure provides an allele of the rice HPS1 gene. The allele may be used to identify and cultivate disease-resistant rice varieties, advancing rice breeding and providing new genetic resources for rice germplasm improvement.

To achieve the above objective, the present disclosure provides the following schemes.

The present disclosure provides an application of the allele of the rice HPS1 gene in cultivating disease-resistant rice varieties, where the nucleotide sequence of the allele is as shown in SEQ ID NO. 1 or SEQ ID NO. 2.

The present disclosure provides a primer pair for detecting the allele of the rice HPS1 gene, including an upstream primer with the nucleotide sequence as shown in SEQ ID NO. 6 and a downstream primer with the nucleotide sequence as shown in SEQ ID NO. 7; and the nucleotide sequence of the allele is as shown in SEQ ID NO. 2.

The present disclosure provides the application of the above primer pair in identifying rice disease resistance.

Optionally, the disease resistance includes the ability to resist diseases caused by fungi and the ability to resist diseases caused by bacteria.

Optionally, the fungi include pathogens causing rice blast and/or pathogens causing sheath blight; and
    the bacteria include pathogens causing bacterial leaf blight.

The present disclosure provides a molecular marker associated with rice disease resistance, where the molecular marker is as shown in SEQ ID NO. 3, with a deletion of 192 base pairs (bp) starting from the 86th position.

The present disclosure provides a primer pair for detecting the above molecular marker, including an upstream primer with the nucleotide sequence as shown in SEQ ID NO. 4 and a downstream primer with the nucleotide sequence as shown in SEQ ID NO. 5.

The present disclosure provides an application of the above molecular marker or the above primer pair in one or more of the following:
    (1) identifying rice disease resistance;
    (2) screening disease-resistant rice varieties;
    (3) improving rice germplasm resources; and
    (4) assisting in rice breeding.

The present disclosure provides a method for identifying rice disease resistance, including the following steps: using the genomic DNA of a sample to-be-tested as template DNA, mixing with the above primer pair for polymerase chain reaction (PCR) amplification; if the PCR product has one DNA band at 200 bp-300 bp and no DNA band at 400-500 bp, it indicates that the sample to-be-tested is a rice variety with high disease resistance; if there is one DNA band at 400-500 bp and no DNA band at 200 bp-300 bp, it indicates that the sample to-be-tested is a rice variety with low disease resistance.

The present disclosure discloses the following technical effects.

The present disclosure provides an allele of the rice HPS1 gene. The allele is a natural excellent allele of the HPS1 gene that may enhance rice resistance to multiple diseases. In specific implementation of the present disclosure, to explore the application value of the HPS1 gene in rice breeding, the inventors analyze 33 high-quality assembled rice genomes and find a structural variation with a 192 bp deletion on the HPS1 gene promoter in 8 of the 33 rice varieties with excellent agronomic traits (such as 93-11). According to the present disclosure, this structural variation enhances the activity of the HPS1 gene promoter and appropriately increases the expression level of the HPS1 gene in rice. The present disclosure further discovers that the natural excellent allele of the HPS1 gene with the structural variation may endow stronger resistance to various fungal and bacterial pathogens, such as rice blast, sheath blight, and bacterial leaf blight. Moreover, the natural excellent allele of the HPS1 gene does not affect plant growth and yield. In specific embodiments of the present disclosure, rice with the HPS1 gene promoter containing the structural variation shows no significant differences in key growth and yield traits, such as plant height, tiller number per plant, 1000-seed weight, grain number per panicle, and seed-setting rate, compared to rice without the HPS1 gene promoter containing the structural variation. Therefore, the natural excellent allele of the HPS1 gene does not adversely affect plant growth and yield, making it valuable for breeding high-yield rice varieties with enhanced disease resistance.

Moreover, the present disclosure identifies a natural structural variation with a 192 bp fragment deletion in the promoter of the HPS1 gene allele from rice resources with excellent agronomic traits, such as the 93-11 variety. Based on this, a molecular marker primer for assisted breeding is developed to screen rice varieties of excellent alleles of the HPS1 gene containing natural structural variation. Using this molecular marker, the present disclosure further discovers that the excellent allele of the HPS1 gene containing natural structural variation may appropriately increase the expression level of the HPS1 gene and enhance rice resistance to various fungal and bacterial pathogens such as rice blast, sheath blight, and bacterial leaf blight. Since few natural excellent alleles resistant to various pathogens have been identified in plants, the present disclosure provides a directly usable molecular marker for breeding high-yield crops with stronger resistance to multiple diseases by screening natural resources.

BRIEF DESCRIPTION OF THE DRAWINGS

In order to explain the embodiments of the present disclosure or the technical solution in the prior art more clearly, the drawings needed in the embodiments will be briefly introduced below. Apparently, the drawings in the following description are only some embodiments of the present disclosure. For one of ordinary skill in the art, other drawings may be obtained according to these drawings without creative effort.

FIG. 3A shows the representative lesion photos and lesion length statistics (mean±s.d., n=15 lesions) of plants of 3-week-old NIP, 93-11, and their RILs 7 days after inoculation with *Magnaporthe oryzae* (physiological race CD27).

Figure 3A:
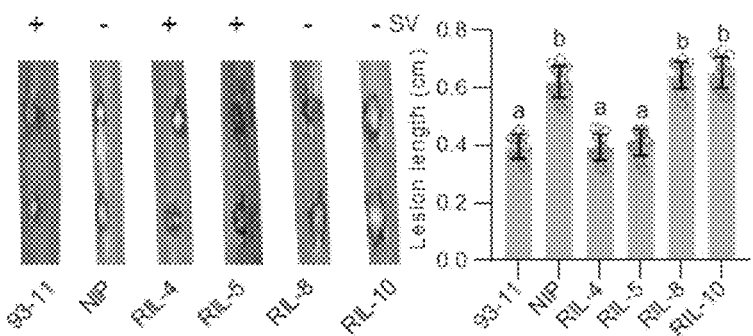
Figure 3B:
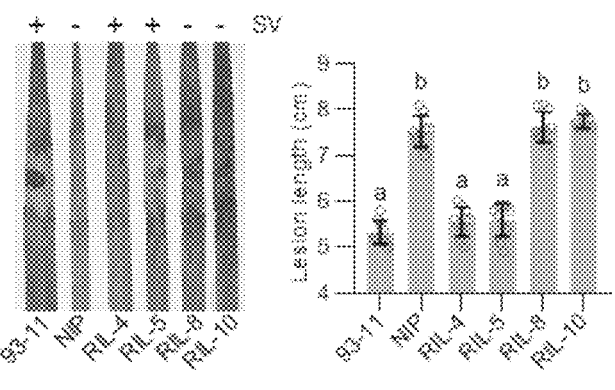

FIG. 3B shows typical lesion photos and lesion length statistics (mean±s.d., n=10 lesions) of plants of tillering-stage NIP, 93-11, and their RILs 2 days after inoculation with *Rhizoctonia solani* (physiological race AG-1-IA).

Figure 3C:
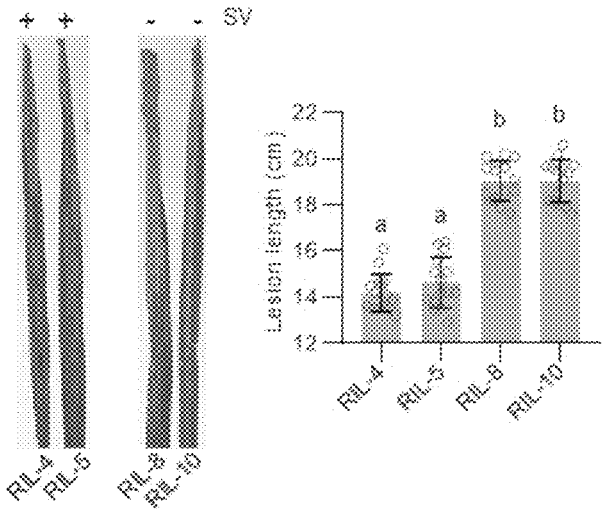

FIG. 3C shows representative lesion photos and lesion length statistics (mean±s.d., n=15 lesions) of plants of RILs of 3-week-old NIP and 93-11 14 days after inoculation with *Xanthomonas oryzae* (physiological race PXO99A). Different letters above the bar chart indicate significant differences (P<0.01), with a scale bar of 1 centimeter (cm). "+" indicates SV-type HPS1, and "−" indicates non-SV-type HPS1.

Figure 4A:
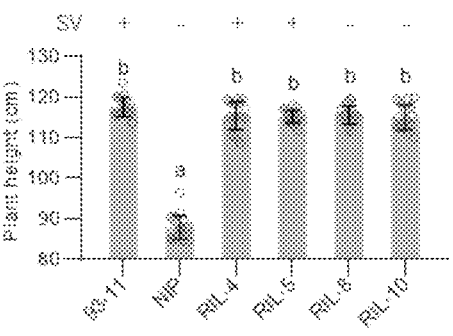

FIG. 4A shows the identification of the effect of SV of the HPS1 on plant height during the maturity stage of plants of NIP, 93-11, and their RILs.

Figure 4B:
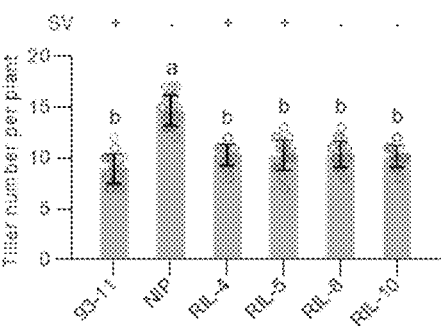

FIG. 4B shows the identification of the effect of SV of the HPS1 on tiller number per plant during the maturity stage of plants of NIP, 93-11, and their RILs.

Figure 4C:
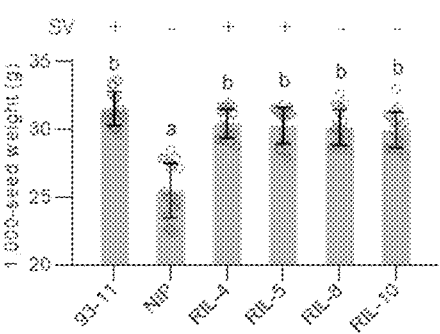

FIG. 4C shows the identification of the effect of SV of the HPS1 on 1000-seed weight during the maturity stage of plants of NIP, 93-11, and their RILs.

Figure 4D:
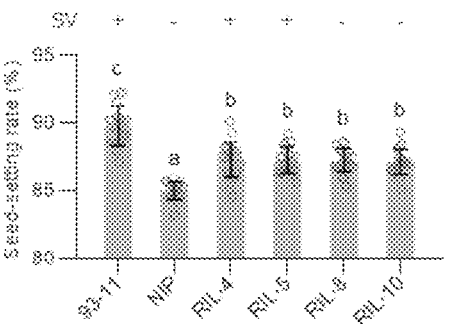

FIG. 4D shows the identification of the effect of SV of the HPS1 on seed-setting rate during the maturity stage of plants of NIP, 93-11, and their RILs.

Figure 4E:
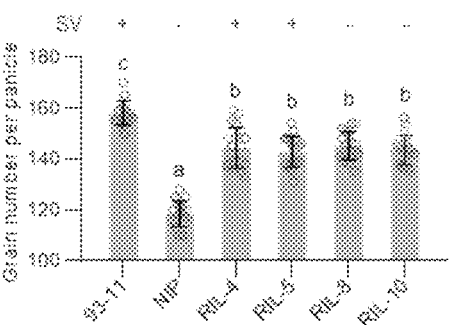

FIG. 4E shows the identification of the effect of SV of the HPS1 on grain number per panicle during the maturity stage of plants of NIP, 93-11, and their RILs. The data in these graphs are the mean±s.d., with n=20 replicates. Different letters above the bar chart indicate significant differences (P<0.01), with "+" indicating SV-type HPS1, and "−" indicating non-SV-type HPS1.

Figure 5:
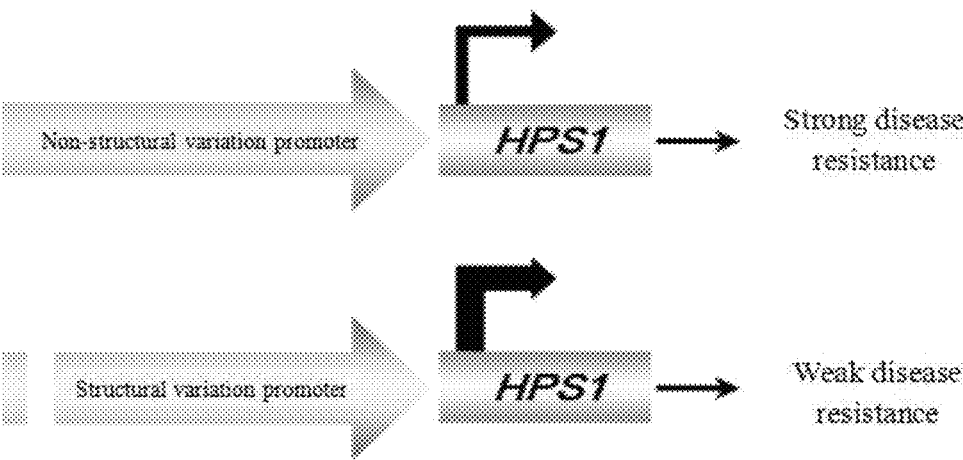

FIG. 5 is a schematic diagram illustrating the mechanism by which the HPS1 excellent allele enhances rice disease resistance. The allele of the HPS1 gene with natural structural variation of 192 bp deletion may appropriately over-express the HPS1 gene in rice, thereby enhancing rice resistance to various diseases.

DETAILED DESCRIPTION OF THE EMBODIMENTS

The present disclosure will now be described in detail through various exemplary embodiments. This detailed description should not be construed as limiting the present disclosure but rather as providing a more detailed explanation of certain aspects, features, and embodiments of the present disclosure.

It should be understood that the terms used herein are for the purpose of describing specific embodiments and are not intended to limit the present disclosure. Additionally, for numerical ranges in the present disclosure, it should be understood that each intermediate value between the upper and lower limits of the range is also specifically disclosed. Any stated value or intermediate value within the stated range, as well as any smaller range formed by any intermediate value within the stated range, is also included in the present disclosure. The upper and lower limits of these smaller ranges may be independently included or excluded from the range.

Unless otherwise specified, all technical and scientific terms used herein have the same meanings as commonly understood by one of ordinary skill in the art to which this invention belongs. Although only preferred methods and materials are described herein, any methods and materials similar or equivalent to those described may also be used in the practice or testing of the present disclosure. All publications mentioned herein are incorporated by reference to disclose and describe the methods and/or materials related to the publications. In case of conflict with any incorporated publication, the content of this specification shall prevail.

Various modifications and changes may be made to the specific embodiments described in this specification without departing from the scope or spirit of the present disclosure, as will be apparent to those skilled in the art. Other embodiments derived from the description of the present disclosure will also be apparent to those skilled in the art. The description and embodiments herein are illustrative only.

The terms "comprising," "including," "having," "containing," and the like used herein are open-ended terms, meaning including but not limited to.

The following embodiments use commercially available pGreenII-0800 vectors and publicly available *Magnaporthe oryzae* (physiological race CD27), *Rhizoctonia solani* (physiological race AG-1-IA), *Xanthomonas oryzae* (physiological race PXO99A), and rice materials (Nipponbare, 93-11, and recombinant inbred lines derived from Nipponbare (NIP) and 93-11) provided and maintained by the State Key Laboratory of Crop Gene Exploration and Utilization in Southwest China at Sichuan Agricultural University.

Figure 1A:
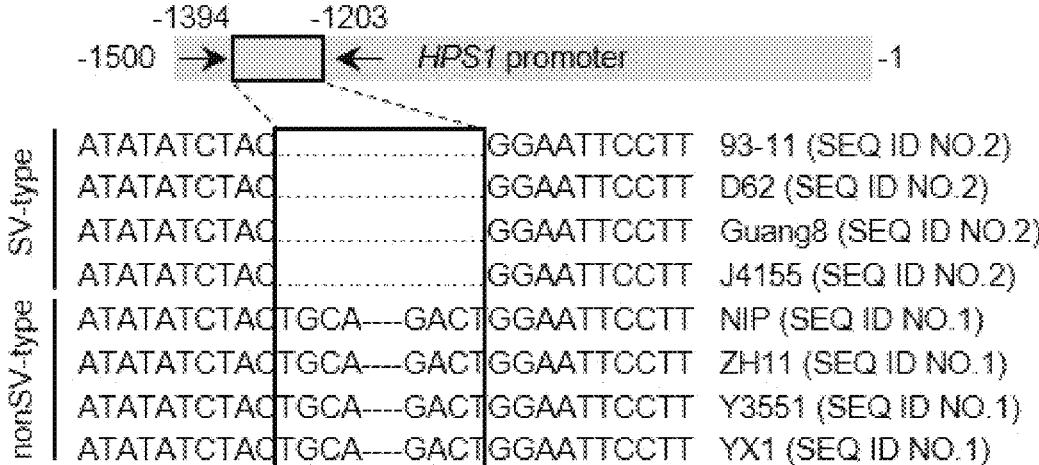
FIG. 1A is a schematic diagram showing the position and sequence comparison of the structural variations in the promoters of the hydrogen peroxide sensor 1 (HPS1) genes in different rice varieties on the genomes, with the box indicating the structural variation with a 192 base pairs (bp) deletion and the black arrows indicating the position of the primer designed for specifically detecting the 192 bp deletion using PCR detection. Y3551 represents Yihui3551, and YX1 represents Yixiang1.

Embodiment 1: Discovery of the Natural Excellent Allele of the Hydrogen Peroxide Sensor 1 (HPS1) Gene To explore the application value of the HPS1 gene (gene ID: Os01g0196300) in rice breeding, the inventors search and analyze 34 high-quality assembled rice genomes (methods and genomes refer to P. Qin et al., *Pan-genome analysis of* 33 *genetically diverse rice accessions reveals hidden genomic variations. Cell,* 184(13): 3542-3558, 2021) and the published *Nipponbare* genome. The results show that in 8 out of 34 rice varieties with excellent agronomic traits (93-11, D62, Wushansimiao, Tumba, Shuhui548, J4155, Guang8, and Y58S), a structural variation (SV) with a 192 base pairs (bp) deletion (−1203 to −1394 bp) is found in sequence of the promoter of HPS1 of the first 1500 bp of the coding region of HPS1 gene. However, no obvious variation is found in the basic domain region (1233 to 1322 bp) (FIG. 1A). This indicates that the promoter of the HPS1 gene has two different nucleotide sequences in rice materials: a non-structural variation type (non-SV type) and a structural variation type (SV type).

The genomic sequence (SEQ ID NO. 1) of the 1500 bp non-SV type HPS1 gene in materials such as NIP, Zhonghua 11 (ZH11), Yixiang1, Yihui3551, Tsipala Menahar, R527, Shuhui498, Nam Roo, Nagina22, Lijiang Xintuan Hei Gu, Lemont, Kongyul31, Koshihikari, IR64, Gui630, Gang46, FS32, Fuhui838, Daohuaxiang2hao, Digu, Chuannongl, Basmatil, 2428, MSU, 1132, and MALAGKIT is as follows:

```
>NC_029256.1: 5202088-5200589 Oryza sativa Japonica Group cultivar
Nipponbare chromosome 1, IRGSP-1.0:
TAATTTGTTGGGATTAGTCATCGTCATGTAACGACTTGCACAACAAACTC

ATTTCTAATTTGCTCTCTCTTTGTTTTGCCGCCGCCCACGCAATGTATATATCTACTG

CAGATTCCTTCCATGCATGCATCTTAATTAACTTCTCCGAATTCATGGATTCCAAATG

AATAATGAATAAGATGCTAAGCTAGGTTTACCAATTAATTGGCTAATTGGCAACCAA

ATGGCTAATCATCATCACCATCATGGCATCATCATCAAATTTTCTAAACGTTGCACC

GGAAAATCAACCTAGACTGGAATTCCTTCCAATCCTTCGCTATAGCTAGCTAGCTAC

CACAACGATCCAAAAGTTTTGTCAAATATTTAGAACGGGGATAGCTAGGCAGTGTC

GACGAAGATGTGATGTGATCTCTGAATATCTGAACCGTCGTCTGATCCACAAAAAGC

TTCCCGGCTCCGGACGCTAGCTGCTCCATCCCATCAATTCTCTCCATTCTCGCTTGCA

TCCAGCCAAACCAAATTGACCGTGGACTGATCACATTTATACTGCTACATCATCCGC

CGTTAATATATATTTTGAGAGACCATATCATTGATAGATACATGCATGCATCCTACT

AATTCGCCCAGATCAACGGCCGGTCTCGAGACGTACTCGCCGGTAATTTGCCGGAA

ATTGTTATACGTTTTCCAAGGGAAGATGTCTTTTTTTATGCCATCTAAATAGTTATGA

AACATTTTGATTAATTTTCTTTTCACGGGATAGATTAATATACGATATGTATCACTCT

GTAAATATGCATGTTCAGAATTTCAACCCCTACATGTTATTGTAAAATGATAAATAT

GACTGTGAAAATGCGTAGACTAGTAGAGTTTTTTTTTTCATTTTGTTACAATGCAACT

TGGTATTCATGTTTGTAAAGTAATATATCTCATATTAATATATCTTATAAAAAATTAT

ATTTTTAAGTTATTTTGGTGGCTTACAAGAAACGATGGGATCGATATATTCCTTCGA

GGGGAAAACAAGGAACATTTCCCAATTTGCCATTAATCTACTCTCACTCATCACAGT

CATCATGCTAGTTGATCTGCACGCTGATCCGATCCGGCCGGAAATTTCGAACTTAAT

TAGCACGTGGATTAATTAGTTGGCAAAAGCTAAGTACAAGTCATTGTGTGGTCAATT

GATCGACTGATCTGTTGCTCCCCGCTTCTGCGGCTTTCATTGGCTATAAATACGCAG

ATATGTGCTCACTGCCTAGCTACCAGTCTTGCATCTCTAACTATATATACACATACAT

GTAGCATCCTGCTCCATCTTAACTAGCTACTACTAGTGATGAGCAGAATCAACCTCA

TGCAGTAATATGCTGTGCTGATCGAATTAATTTACACATATATAGATAGATAGATAG
```

ATAGATCGTTCGACCAATCGAGCTAGCTTGAGCAAACTGATTGACCTGGTGAAGTG

GTATAATTAACGAGCAGATC (nonSV-type HPS1).

The genomic sequence (SEQ ID NO. 2) of the 1500 bp SV-type HPS1 gene in materials such as 93-11, D62, Wushansimiao, Tumba, Shuhui548, J4155, Guang8, and Y58S, with the 192 bp deletion indicated by dotted lines, is as follows:

TAATTTGTTGGGATTAGTCATCGTCATGTAACGACTTGCACAACAAACTC

ATTTCTAATTTGCTCTCTCTTTGTTTTGCCGCCGCCCACGCAATGTATATATCTAC......

...........................................................

...........GGAATTCCTTCCAATCCTTCGCTATAGCTAGCTAGCTACCACAACG

ATCCAAAAGTTTTGTCAAATATTTAGAACGGGGATAGCTAGGCAGTGTCGACGAAG

ATGTGATGTGATCTCTGAATATCTGAACCGTCGTCTGATCCACAAAAAGCTTCCCGG

CTCCGGACGCTAGCTGCTCCATCCCATCAATTCTCTCCATTCTCGCTTGCATCCAGCC

AAACCAAATTGACCGTGGACTGATCACATTTATACTGCTACATCATCCGCCGTTAAT

ATATATTTTGAGAGACCATATCATTGATAGATACATGCATGCATCCTACTAATTCGC

CCAGATCAACGGCCGGTCTCGAGACGTACTCGCCGGTAATTTGCCGGAAATTGTTAT

ACGTTTTCCAAGGGAAGATGTCTTTTTTTATGCCATCTAAATAGTTATGAAACATTTT

GATTAATTTTCTTTTCACGGGATAGATTAATATACGATATGTATCACTCTGTAAATAT

GCATGTTCAGAATTTCAACCCCTACATGTTATTGTAAAATGATAAATATGACTGTGA

AAATGCGTAGACTAGTAGAGTTTTTTTTTTCATTTTGTTACAATGCAACTTGGTATTC

ATGTTTGTAAAGTAATATATCTCATATTAATATATCTTATAAAAAATTATATTTTTAA

GTTATTTTGGTGGCTTACAAGAAACGATGGGATCGATATATTCCTTCGAGGGGAAAA

CAAGGAACATTTCCCAATTTGCCATTAATCTACTCTCACTCATCACAGTCATCATGCT

AGTTGATCTGCACGCTGATCCGATCCGGCCGGAAATTTCGAACTTAATTAGCACGTG

GATTAATTAGTTGGCAAAAGCTAAGTACAAGTCATTGTGTGGTCAATTGATCGACTG

ATCTGTTGCTCCCCGCTTCTGCGGCTTTCATTGGCTATAAATACGCAGATATGTGCTC

ACTGCCTAGCTACCAGTCTTGCATCTCTAACTATATATACACATACATGTAGCATCCT

GCTCCATCTTAACTAGCTACTACTAGTGATGAGCAGAATCAACCTCATGCAGTAATA

TGCTGTGCTGATCGAATTAATTTACACATATATAGATAGATAGATAGATAGATCGTT

CGACCAATCGAGCTAGCTTGAGCAAACTGATTGACCTGGTGAAGTGGTATAATTAA

CGAGCAGATC (SV-type HPS1).

The 8 rice varieties with SV-type HPS1 are well-known and have excellent agronomic traits, and these rice varieties are widely used in rice breeding in China.

Embodiment 2: Development of Molecular Marker for the Natural Excellent Allele of the Hps1 Gene The nucleotide sequence of the molecular marker is specifically CGTCATGTAACGACTTGCACAACAAACT-CATTTCTAATTTGCTCTCTCTTTGTTTTGCCGCCGC-CCACGCAATGTATATATCTACTGCAGATTCCTTCCA-TGCATGCATCTTAATT AACTTCTCCGAATTCATGGA-TTCCAAATGAATAATGAATAAGATGCTAAGCTAGG-TT TACCAATTAATTGGCTAATTGGCAACCAAATGG-CTAATCATCATCACCATCATGGCA TCATCATCAAAT-TTTCTAAACGTTGCACCGGAAAATCAACCTAGAC-TGGAATTCCTTCCAATCCTTCGCTATAGCTAGCTA-GCTACCACAACGATCCAAAAGTTTTGTCAAATA TTTAGAACGGGGATAGCTAGGCAGTGTCGACGAA-GATGTGATGTGATCTCTGAATA TCTGAACCGTCG-TCTGATCCACAAAAAGCTTCCCGGCTC (SEQ ID NO. 3), with a 192 bp deletion starting from the 86th position.

To develop a molecular marker that may detect natural structural variation with a 192 bp deletion in the HPS1 gene, the inventors design a specific primer on the HPS1 gene (the primer is shown in Table 1).

TABLE 1

Primer sequences for molecular marker based on HPS1 structural variation

| Primer name | | Primer sequence (5'-3') | SEQ ID NO. |
|---|---|---|---|
| HPS1-SV-detection | Upstream primer | CGTCATGTAACGACTTGCACA | 4 |
| | Downstream primer | GAGCCGGGAAGCTTTTTGTG | 5 |

After the genomes of 93-11, D62, NIP and ZH11 rice materials are extracted, PCR experiments are carried out. The PCR system is shown in Table 2.

TABLE 2

PCR reaction system

| Component | Dosage |
|---|---|
| 10 × PCR Buffer | 2.5 microliters (μL) |
| MgSO₄ (2 millimolar (mM)) | 1.5 μL |
| dNTP (2.5 mM each) | 2.5 μL |
| 50% glycerol | 2.5 μL |
| Forward primer (10 micromolar (μM)) | 0.2 μL |
| Reverse primer (10 μM) | 0.2 μL |
| KOD-Plus Polymerase | 0.5 μL |
| Genome | 1.0 μL |
| ddH₂O | 14.1 μL |
| Total | 25 μL |

The above samples are mixed evenly and centrifuged for PCR reaction, and the PCR amplification is carried out by falling PCR. The reaction procedure is as follows:

TABLE 3

PCR reaction procedure

| Temperature | Time | Cycle |
|---|---|---|
| 95 degrees Celsius (° C.) | 5 minutes (min) | |
| 95° C. | 30 seconds (sec) | |
| 58° C. | 30 sec | 28-34 cycles |
| 68° C. | 30 sec (~1 kilobase per minute (kb/min)) | |
| 68° C. | 10 min | |
| 4° C. | Storage | |

Figure 1B:
FIG. 1B shows molecular marker detection results of the HPS1 structural variations in different rice varieties, where the smaller DNA fragment indicates a natural structural variation of 192 bp deletion in HPS1 in this variety.

Afterwards, electrophoresis is performed, and the result is shown in FIG. 1B. In this embodiment, the fragment size amplified from 93-11 and D62 rice materials using the primer in Table 1 is 247 bp, while the fragment size amplified from NIP and ZH11 rice materials is 439 bp. This result indicates that the HPS1 gene in 93-11 and D62 materials is of the SV-type HPS1 genomic sequence (SEQ ID NO. 2), with a 192 bp deletion compared to the non-SV type HPS1 gene, proving the effectiveness and accuracy of this molecular marker.

Embodiment 3: Identification of the Regulatory Effect of the Natural Excellent Allele of The HPS1 Gene on Promoter Activity Promoter activity controls gene transcription, while structural variations on the promoter may affect the promoter activity. To identify the effect of the 192 bp deletion (SV) on the activity of the HPS1 gene, the inventors select to express pGreenII-0800 plasmids carrying the HPS1 gene from different rice varieties in rice protoplasts. The functional principle of the pGreenII-0800 binary vector is that, on the one hand, it may overexpress the Renilla luciferase (RLUC) gene as an internal reference through the 35S promoter, and on the other hand, it may insert the luciferase (LUC) gene expressed through a custom promoter. By comparing the relative ratio of LUC to RLUC, the relative activity of the custom-inserted promoter may be understood.

The inventors use the primers in Table 4 to construct pGreenII-0800 plasmids carrying different HPS1 genes inserted into 93-11, D62, NIP, and ZH11 rice varieties. These plasmids are then transferred into prepared rice protoplasts for expression for 24 hours (h) (method reference: He F. et al., *Rice protoplast isolation and its application for transient expression analysis, Curr. Protoc. Plant Biol.* 1(2): 373-383, 2016), and the relative activity ratio of LUC to RLUC is measured.

TABLE 4

Primer sequences related to HPS1 gene

| Primer name | | Primer sequence (5'-3') | SEQ ID NO. | Use |
|---|---|---|---|---|
| pGreenII-0800-HPS1 | Upstream primer | TTGATATCGAATTCCTGCAG TAATTTGTTGGGATTAGTCA | 6 | Constructing pGreenII-0800 plasmids carrying HPS1 genes of different rice varieties |
| | Downstream primer | GCTCTAGAACTAGTGGATCC GATCTGCTCGTTAATTATAC | 7 | |

TABLE 4-continued

| Primer sequences related to HPS1 gene | | | | |
|---|---|---|---|---|
| Primer name | | Primer sequence (5'-3') | SEQ ID NO. | Use |
| qHPS1 | Upstream primer | GGCAACAACGGCTTCATGTG | 8 | Detecting expression |
| | Downstream primer | TGAGGTGGTGCTCAATCTGC | 9 | level of HPS1 gene in rice plants |

Figure 2A:
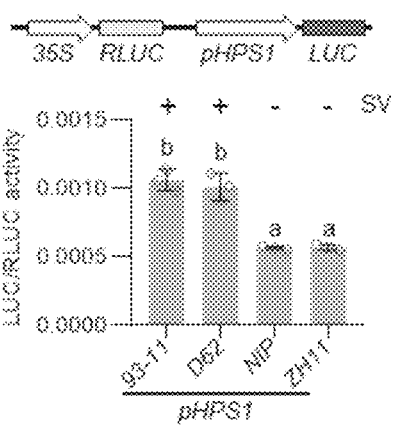
FIG. 2A shows the detection of HPS1 activity in different rice varieties using luciferase activity assay (mean±s.d., n=3 replicates).

The results are shown in FIG. 2A. The relative activity of SV-type HPS1 (allele of the HPS1 gene) in rice varieties 93-11 and D62 is significantly higher than that of nonSV-type HPS1 (the HPS1 gene) in varieties NIP and ZH11, indicating that the presence of structural variation (SV) with a 192 bp deletion on the promoter of the HPS1 gene enhances the activity of the HPS1 gene.

Figure 2B:
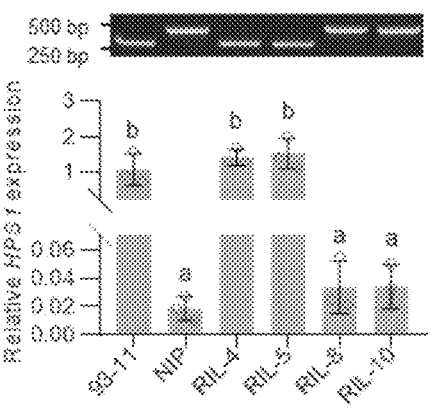
FIG. 2B shows the detection of expression levels of the HPS1 gene in 3-week-old NIP, 93-11, and their recombinant inbred lines (RILs) (mean±s.d., n=3 replicates). "+" indicates SV-type HPS1, and "−" indicates nonSV-type HPS1. The lanes in the electropherogram of FIG. 2B are 93-11, NIP, RIL-4, RIL-5, RIL-8, and RIL-10 from left to right.

Embodiment 4: Identification of the Regulatory Effect of the Natural Excellent Allele of the HPS1 Gene on HPS1 Gene Expression To further verify the function of SV, the inventors cross NIP with 93-11 and obtain a series of RILs. The inventors then successfully identify RILs (where RIL-4 and RIL-5 are plants containing SV-type HPS1, while RIL-6 and RIL-10 are plants containing nonSV-type HPS1) containing different types of HPS1 genes using the developed molecular marker, and detect the expression levels of the HPS1 genes in 93-11, NIP/RIL-4, RIL-5, RIL-6, and RIL-10 plants. Quantitative PCR experiments are performed using the primers in Table 4, and the results are shown in FIG. 2B. The expression levels of the HPS1 genes in inbred lines containing SV-type HPS1 are higher than the expression levels of the HPS1 genes in inbred lines containing nonSV-type HPS1 (FIG. 2B). These results indicate that SV-type HPS1 has stronger activity than nonSV-type HPS1 and may appropriately increase the expression level of the HPS1 gene in rice. The HPS1 gene promoter without the 192 bp deletion may drive the expression of downstream genes at a lower level, while the HPS1 gene promoter with the 192 bp deletion may drive the expression of downstream genes at a higher level.

Embodiment 5: Identification of the Regulatory Effect of the Natural Allele of the HPS1 Gene on Rice Blast Resistance Next, the inventors test the regulatory effect of the HPS1 gene on rice disease resistance. The inventors first prick the leaves of 3-week-old 93-11, NIP, RIL-4, RIL-5, RIL-8, and RIL-10 rice seedlings, and inoculate them with 5 μL of *Magnaporthe oryzae* (physiological race CD27) spore suspension ($5 \times 10^5$ spores/milliliter (mL)), and count the lesion sizes after incubation at 28° C. for 7 days. The results are shown in FIG. 3A. The lesion lengths of RIL-4 and RIL-5 containing SV-type HPS1 are significantly shorter than the lesion lengths of RILs (RIL-8 and RIL-10) containing nonSV-type HPS1.

Embodiment 6: Identification of the Regulatory Effect of the Natural Allele of the HPS1 Gene on Sheath Blight Resistance The inventors place uniformly sized mycelial blocks of strains of *Rhizoctonia solani* (physiological race AG-1-IA)

on rice leaves of tillering-stage 93-11, NIP, RIL-4, RIL-5, RIL-8, and RIL-10 plants (cultured on potato dextrose agar (PDA) medium for 2 days), and count the lesion sizes after incubation at 28° C. for 2 days. The experimental results, as shown in FIG. 3B, indicate that the lesion lengths on RIL-4 and RIL-5 leaves containing SV-type HPS1 are significantly shorter than the lesion lengths on RIL-8 and RIL-10 leaves containing nonSV-type HPS1 (FIG. 3B).

Embodiment 7: Identification of the Regulatory Effect of the Natural Allele of the HPS1 Gene on Bacterial Leaf Blight Resistance The inventors cut the rice leaves of tillering-stage 93-11, NIP, RIL-4, RIL-5, RIL-8, and RIL-10 plants approximately 1 cm from the leaf tip. The scissors used in the experiment are pre-soaked in a bacterial suspension of *Xanthomonas oryzae* (physiological race PXO99A, $OD_{600}$=0.6) (cultured on PDA medium for 2 days), so the wounds on the cut leaves are infected with *Xanthomonas oryzae* and naturally develop the disease. After complete disease development, the lesion sizes are counted. The experimental results are shown in FIG. 3C. After 14 days of inoculation with *Xanthomonas oryzae*, the lesion lengths on RIL-4 and RIL-5 containing SV-type HPS1 are significantly shorter than the lesion lengths on RIL-8 and RIL-10 containing nonSV-type HPS1.

The results of Embodiment 5-Embodiment 7 indicate that rice containing the natural allele of SV-type HPS1 has stronger resistance to various fungal and bacterial diseases.

Embodiment 8: Identification of the Regulatory Effect of the Natural Allele of the HPS1 Gene on Rice Growth and Yield The agronomic traits of 93-11, NIP, RIL-4, RIL-5, RIL-8, and RIL-10 plants are investigated, and the results are shown in FIG. 4A-FIG. 4E. The measurement results show that there are no significant differences in important rice growth and yield traits such as plant height (FIG. 4A), tiller number (FIG. 4B), 1000-seed weight (FIG. 4C), seed-setting rate (FIG. 4D), and grain number per panicle (FIG. 4E) between RIL-4 and RIL-5 containing SV-type HPS1 and RIL-8 and RIL-10 containing nonSV-type HPS1. The above results indicate that SV-type HPS1 has no significant effect on plant growth and yield.

In summary, the present disclosure finds that SV-type HPS1 does not have adverse effects on crop growth and yield when endowing crops with stronger multi disease resistance, and has significant application value for breeding crop varieties with different disease resistance. That is, rice plants containing SV-type HPS1 (structural variation promoter) are strongly disease-resistant rice plants, while rice plants containing nonSV-type HPS1 (non-structural variation promoter) are weakly disease-resistant rice plants (FIG. 5). Moreover, the molecular marker and primer pair for detecting the marker described in the present disclosure have good effectiveness and accuracy, and may be used for identifying rice disease resistance, screening disease-resistant rice varieties, improving rice germplasm resources, and assisting in rice breeding.

The above-mentioned embodiments only describe the preferred mode of the present disclosure, and do not limit the scope of the present disclosure. Under the premise of not departing from the design spirit of the present disclosure, various modifications and improvements made by one of ordinary skill in the art to the technical solution of the present disclosure should fall within the protection scope defined by the claims of the present disclosure.

What is claimed is:

1. A method for identifying rice disease resistance, comprising:

a) extracting genomic deoxyribonucleic acid (DNA) from leaf tissue of a rice plant;

b) amplifying the extracted DNA by polymerase chain reaction (PCR) using a primer pair consisting of SEQ ID NO: 4 and SEQ ID NO: 5;

c) electrophoretically detecting a PCR product; and d) identifying the rice plant as having high disease resistance when the PCR product has one DNA band at 200 bp-300 bp and no DNA band at 400-500 bp as compared to plant having a DNA band at 400-500 bp and identifying the rice plant as having low disease resistance when there is one DNA band at the 400-500 bp and no DNA band at the 200 bp-300 bp as compared to plant having a DNA band at 200-300 bp;

wherein the disease resistance comprises resistance to rice blast, resistance to sheath blight, and resistance to bacterial leaf blight.

* * * * *